US00PP34531P2

(12) United States Plant Patent
Ammerlaan

(10) Patent No.: US PP34,531 P2
(45) Date of Patent: Aug. 30, 2022

(54) ***ECHEVERIA* PLANT NAMED 'OVPEARLS12'**

(50) Latin Name: ***Echeveria pulidonis* x *gibbiflora***
Varietal Denomination: OVPEARLS12

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/803,288

(22) Filed: Apr. 21, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
CPC ... A01H 5/12; A01H 5/00; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct variety of *Echeveria* plant named 'OVPEARLS12' which is characterized by a very large amount of succulent foliage that is tightly held in a compact basal rosette, oblanceolate to narrowly oblong foliage with a very upright attitude, strongly glaucous foliage with a dark blue-grey general coloration, juvenile foliage with apical margins and laminar tips that are lightly suffused with greyed-red, and mature foliage with greyed-orange apical margins and greyed-purple laminar tips. The new variety has shown to be uniform and stable in the resulting generations from asexual propagation.

4 Drawing Sheets

Latin name of the genus and species: The Latin name of the genus and species of the novel variety disclosed herein is *Echeveria pulidonis* x *gibbiflora*.

Variety denomination: The inventive variety of *Echeveria* disclosed herein has been given the variety denomination 'OVPEARLS12'.

BACKGROUND OF THE INVENTION

Parentage: 'OVPEARLS12' is a seedling selection, presumed to be the result of the open pollination of an unnamed *Echeveria pulidonis* plant (unpatented), the seed parent, and a plurality of unnamed *Echeveria gibbiflora* plants (not patented), the presumed pollen parent. The exact pollen parent is unknown. The crossing is believed to have occurred in the summer of 2016 at a commercial greenhouse in Bleiswijk, the Netherlands. In early 2017, one seedling from said cross was observed to exhibit unique foliage and growth characteristics when compared to the parent plants and all other progeny. After confirming the stability of the unique characteristics first observed, the new plant was selected for commercialization and given the name, 'OVPEARLS12'.

Asexual Reproduction: Asexual reproduction of the new cultivar 'OVPEARLS12', by way of rooting leaf cuttings, was first initiated in the autumn of 2017 at the inventor's commercial greenhouse in Bleiswijk, the Netherlands. Through eleven subsequent generations, the unique features of this cultivar have proven to be stable and true to type.

SUMMARY OF THE INVENTION

The cultivar 'OVPEARLS12' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS12'. These characteristics in combination distinguish 'OVPEARLS12' as a new and distinct *Echeveria* cultivar:

1. 'OVPEARLS12' exhibits a very large amount of succulent foliage that is tightly held in a compact basal rosette; and
2. 'OVPEARLS12' exhibits oblanceolate to narrowly oblong foliage with a very upright attitude; and
3. 'OVPEARLS12' exhibits strongly glaucous foliage that is colored green to greyed-green and covered with a layer of greyed-green epicuticular wax which gives the foliage a dark blue-grey general coloration; and
4. 'OVPEARLS12' exhibits juvenile foliage with a greyed-red apical margins and laminar tip; and
5. 'OVPEARLS12' exhibits mature foliage with greyed-orange apical margins and greyed-purple laminar tips.

BOTANICAL DESCRIPTION OF THE PLANT

Figure 1:
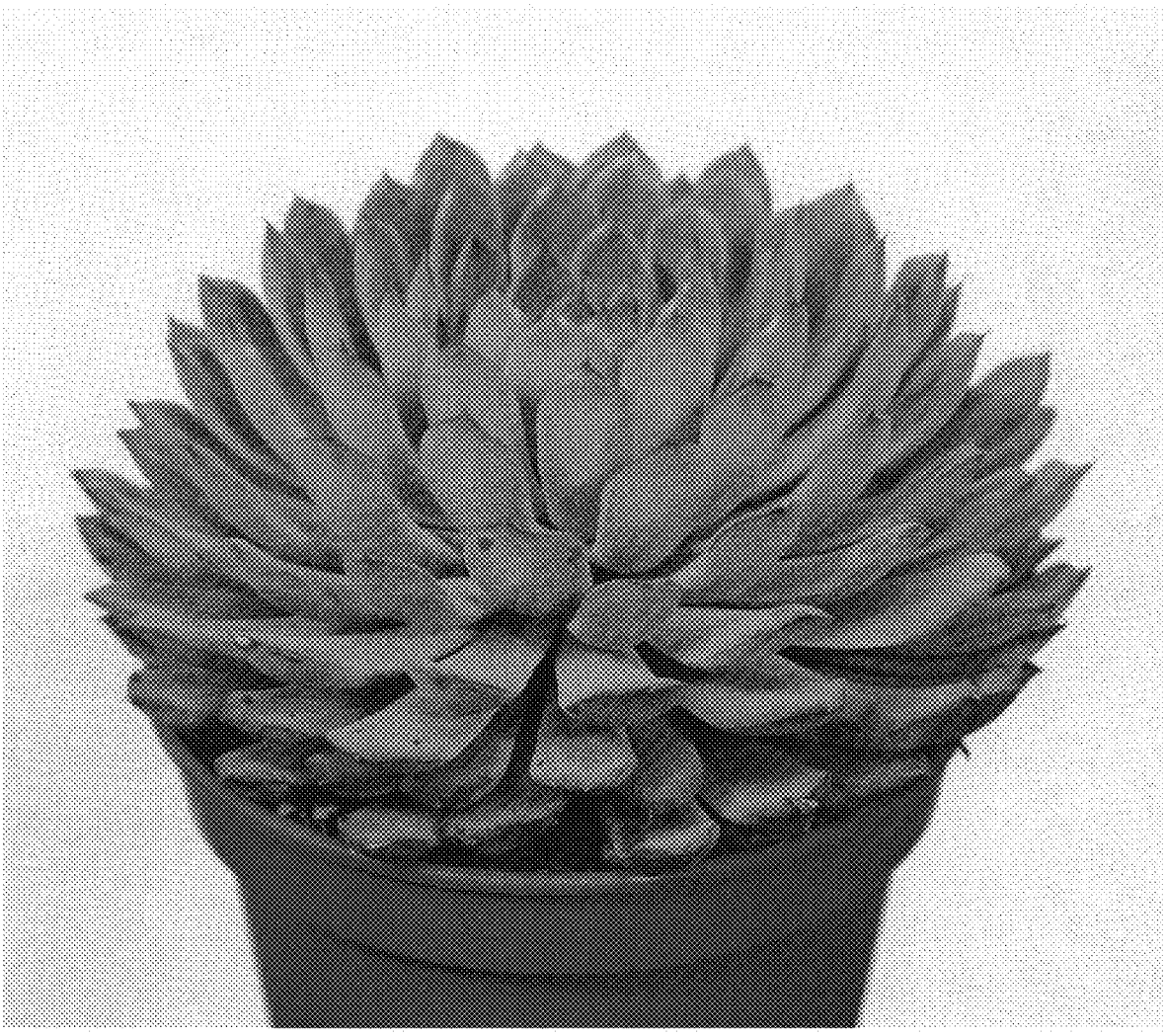
FIG. 1 illustrates, as nearly true as it is reasonably possible to make the same in color photographs of this type, an exemplary plant of 'OVPEARLS12' grown in a commercial greenhouse in Bleiswijk, the Netherlands. This plant is approximately 1.5 year old, shown planted in an 15 cm container.
Figure 2:
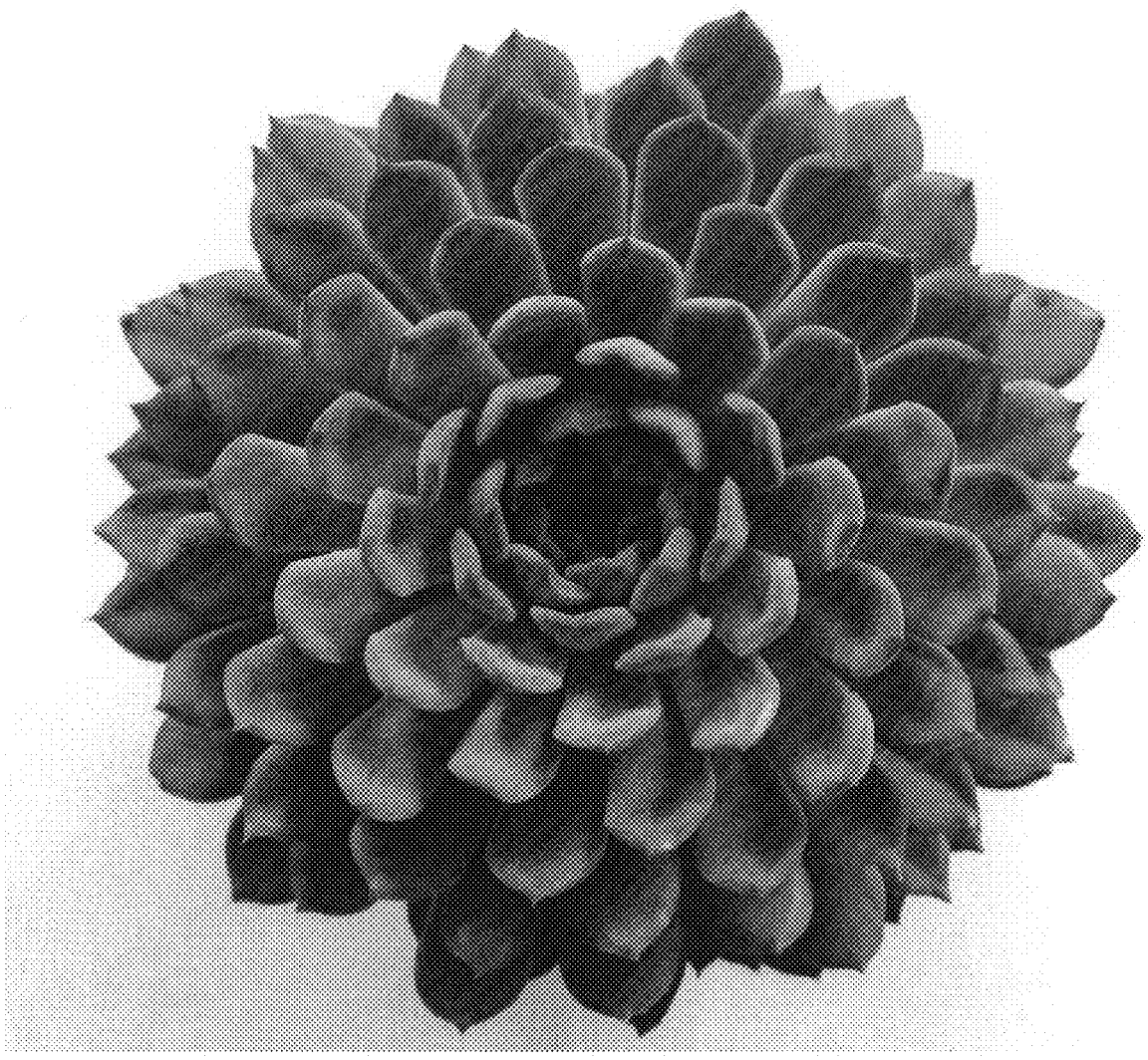
FIG. 2 illustrates, as nearly true as it is reasonably possible to make the same in color photographs of this type, the typical foliage arrangement of 'OVPEARLS12'.
Figure 3:
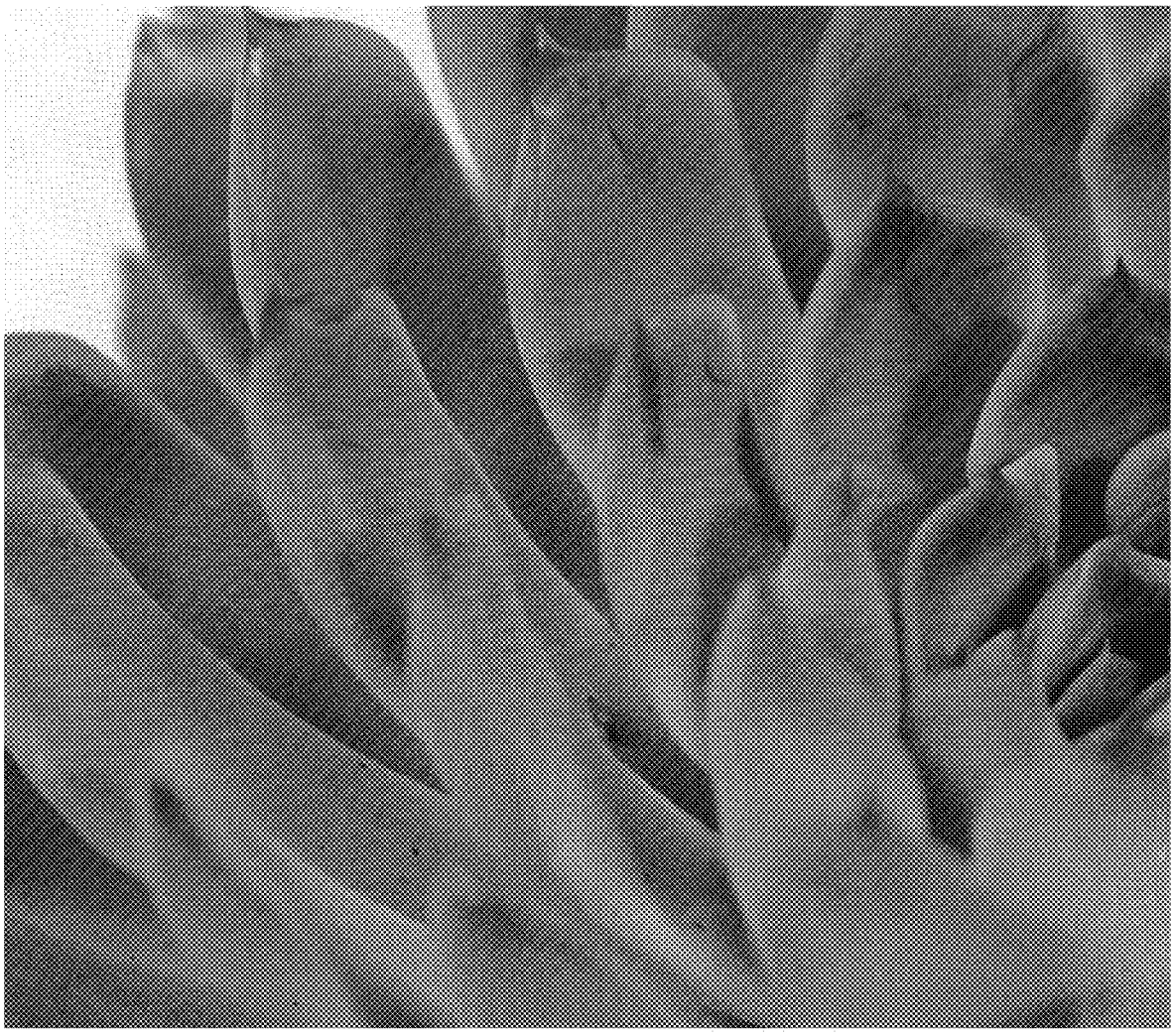
FIG. 3 illustrates, as nearly true as it is reasonably possible to make the same in color photographs of this type, the adaxial surface of the mature foliage 'OVPEARLS12'.
Figure 4:
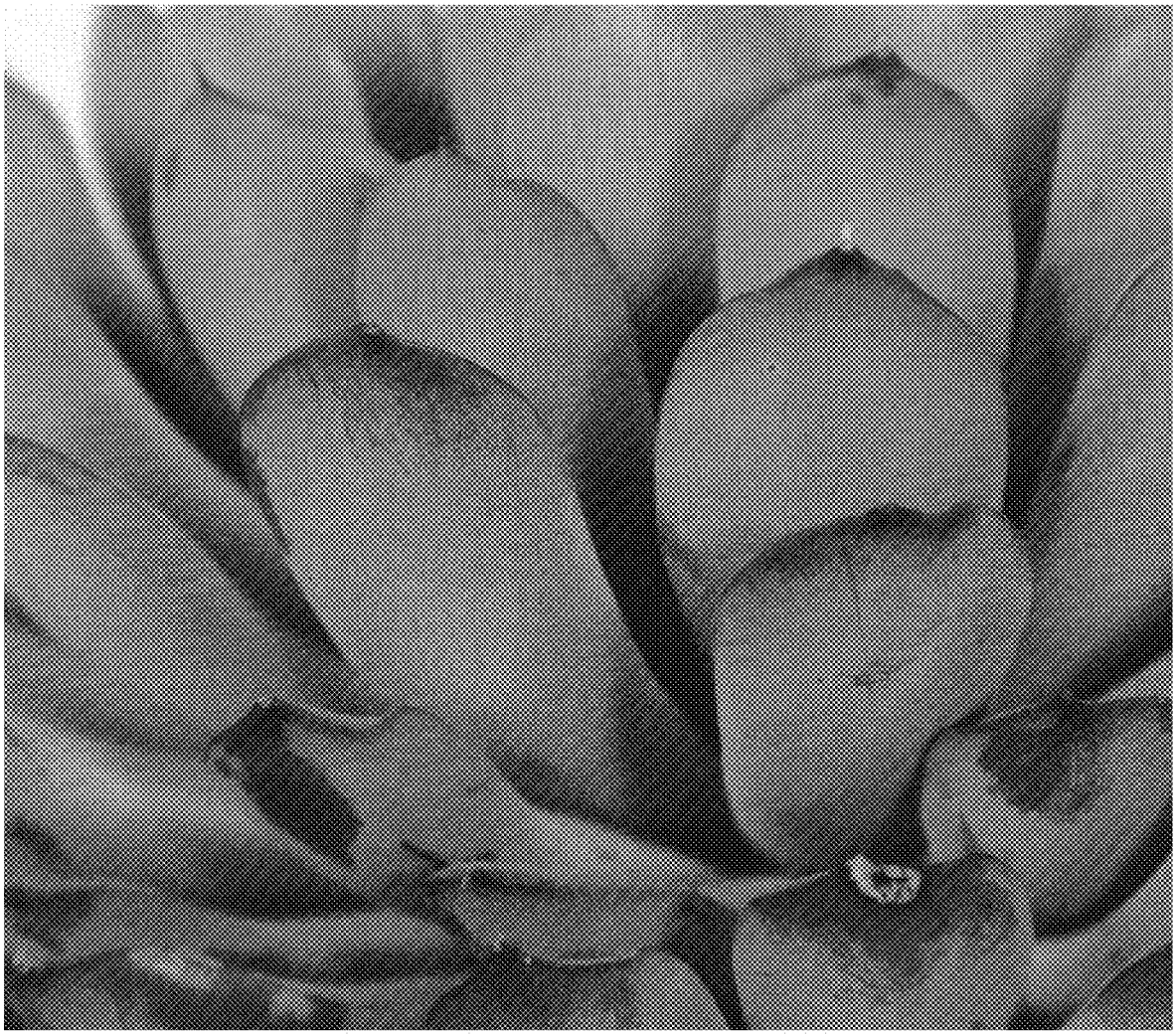
FIG. 4 illustrates, as nearly true as it is reasonably possible to make the same in color photographs of this type, the abaxial surface of the mature foliage 'OVPEARLS12'.

The following observations and measurements made in December of 2021 describe averages from a sample set of six specimens of 1 year old 'OVPEARLS12' plants grown in 8.5 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS12' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Society Colour Chart, The Royal Horticultural Society, London, 2015 (sixth edition).

A botanical description of 'OVPEARLS12' and a comparison with the parent plants and closest known comparator is provided below.

Plant description:

*Growth habit.*—Succulent perennial with foliage growing in a compact, non-branched basal rosette.

*Plant form.*—Flattened globular.

*Height from soil level to top of foliar plane.*—9.5 cm.

*Plant spread.*—Average of 17.6 cm.

*Growth rate.*—Moderately fast.

*Plant vigor.*—Moderately vigorous.

*Propagation.*—Type — Leaf cuttings. Time to initiate rooting — Approximately 5 weeks at an approximate temperature of 21 degrees Celsius. Crop time — Approximately 1 year to produce a marketable plant in a 7 cm container.

*Disease and pest resistance or susceptibility.*—Neither resistance nor susceptibility to typical *Echeveria* pests and diseases has been observed.

*Environmental tolerances.*—Adapt to, at least, USDA Zones 10 to 12 and temperatures as high as 40 degrees Celsius; moderate tolerance to rain yet drought tolerant once established; high tolerance to wind.

Root system:

*General.*—Fine, well-branched fibrous roots.

Stems:

*Branching habit.*—Leaves in a non-branching basal rosettes; no main branches or lateral branches present.

Foliage:

*Arrangement.*—Rosette.

*Division.*—Simple.

*Attachment.*—Sessile.

*Quantity.*—Approximately 160 leaves per rosette.

*Shape.*—Oblanceolate to narrowly oblong.

*Dimensions.*—7.3 cm long, 1.9 cm wide, and 0.8 cm thick, on average.

*Aspect.*—Very slightly concave; distalmost portion of the lamina is slightly curled upward at an average angle of 30 degrees.

*Attitude.*—Juvenile foliage at the center of the rosette exhibits a near-vertical attitude; foliage becomes progressively more relaxed as it matures and becomes nearly horizontal to slightly pendulous at the outer whorls of the rosette.

*Apex.*—Apiculate.

*Base.*—Long cuneate.

*Margin.*—Entire; occasionally with some slight undulation along one side of the lamina, at and near the apex.

*Pubescence, texture and luster of the adaxial surface.*—Glabrous, smooth, and matte; strongly glaucous.

*Pubescence, texture and luster of the abaxial surface.*—Glabrous, smooth, and matte; strongly glaucous.

*Color.*—Juvenile foliage, adaxial surface — Green, nearest to RHS NN137D; fading to yellow-green towards the base, nearest to RHS 146D; margined with a lighter shade of yellow-green, nearest to a combination of RHS 145C and 145D; apical margins and laminar tip are lightly suffused with greyed-red, nearest to RHS 182A. Leaves are covered with a thin layer of epicuticular wax which is colored greyed-green, nearest to RHS N189C. Juvenile foliage, abaxial surface — Greyed-green, nearest to a combination of RHS 191A and 191B; fading lighter towards the base, nearest to RHS 193A; margined yellow-green, nearest to a mixture RHS 145C and 145D; apical margins and laminar tip are lightly suffused with greyed-red, nearest to RHS 182A. Leaves are covered with a thin layer of epicuticular wax which is colored greyed-green, nearest to a mixture of RHS N189C and N189D. Mature foliage, adaxial surface — Nearest to a mixture of green and greyed-green, RHS NN137D and 191A; fading to yellow-green towards the base, nearest to RHS 147C; apical margins are greyed-orange, nearest to RHS 176B; laminar tip is greyed-purple, RHS N186C. Leaves are covered with a thin layer of epicuticular wax which is colored greyed-green, nearest to RHS N189C. Mature foliage, abaxial surface — Nearest to a mixture of yellow-green and greyed-green, RHS 148B and 197A; fading to yellow-green towards the base, nearest to a combination of RHS N148A and N148B; apical margins are greyed-orange, nearest to in between RHS 176A and 176B; laminar tip is greyed-purple, RHS N186C. Leaves are covered with a thin layer of epicuticular wax which is colored greyed-green, nearest to a mixture of RHS 189C and 189D.

*Venation.*—Pattern — No venation is visible. Color, adaxial surface — No venation is visible. Color, abaxial surface — No venation is visible.

*Petiole.*—No petiole; leaves are sessile.

Inflorescence: No flowering has been observed to date.

Comparisons with the parent plant: Plants of the new cultivar 'OVPEARLS12' differ from the seed parent, an unnamed *Echeveria pulidonis* plant (not patented) in the following characteristics described in Table 1 below.

TABLE 1

| Characteristic | 'OVPEARLS12' | The seed parent. |
|---|---|---|
| Foliage length. | Longer than the seed parent' | Shorter than 'OVPEARLS12'. |
| Foliage width. | Narrower than the seed parent. | Broader than 'OVPEARLS12'. |
| General coloration of the foliage. | Dark blue-grey. | Nearest to a mixture of blue-grey and greyed-green. |

Plants of the new cultivar 'OVPEARLS12' differ from the pollen parent, an unnamed *Echeveria gibbiflora* plant (not patented) in the following characteristics described in Table 2 below.

TABLE 2

| Characteristic | 'OVPEARLS12' | The pollen parent. |
|---|---|---|
| Foliage abundance. | More abundant than the pollen parent. | Less abundant than 'OVPEARLS12'. |
| Foliage shape. | Oblanceolate to narrowly oblong. | Broadly obovate. |
| General coloration of the foliage | Dark blue-grey. | Blue-grey and heavily suffused with red-purple. |

Comparisons with the closest known comparator: Plants of the new cultivar. 'OVPEARLS12' differ from *Echeveria* hybrid 'OVPEARLS14' (U.S. Plant patent application Ser. No. 17/803,289 filed concurrently), which is the closest known comparator, in the following characteristics described in Table 3 below.

TABLE 3

| Characteristic | 'OVPEARLS12' | 'OVPEARLS14' |
|---|---|---|
| Plant size. | Smaller than 'OVPEARLS14'. | Larger than 'OVPEARLS12'. |
| Foliage abundance. | More abundant than 'OVPEARLS14'. | Less abundant than 'OVPEARLS12'. |
| Foliage shape. | Oblanceolate to narrowly oblong. | Oblanceolate. |
| Foliage size. | Smaller than 'OVPEARLS14'. | Larger than 'OVPEARLS12'. |
| Foliar margins. | Occasionally with some slight undulation along one side of the lamina, at and near the apex. | Occasionally very lightly crenulate to denticulate, usually along one side of the lamina, at and near the apex. |

That which is claimed is:

1. A new and distinct variety of *Echeveria pulidonis* x *gibbiflora* plant named 'OVPEARLS12', substantially as described and illustrated herein.

* * * * *